United States Patent [19]

Szemler et al.

[11] Patent Number: 4,752,584

[45] Date of Patent: Jun. 21, 1988

[54] PROCESS FOR THE PRODUCTION OF INOCULUM FOR ANAEROBIC FERMENTATION OF COENZYME $B_{12}$

[75] Inventors: László Szemler; Eva C. Pechány, both of Budapest, Hungary

[73] Assignee: Richter Gedeon Vegyeszeti Gyar R.T., Budapest, Hungary

[21] Appl. No.: 648,794

[22] Filed: Sep. 7, 1984

[30] Foreign Application Priority Data

Sep. 16, 1983 [HU] Hungary ............................ 3209/83

[51] Int. Cl.$^4$ ........................ C12N 1/20; C12P 19/42
[52] U.S. Cl. ........................................ 435/253; 435/86
[58] Field of Search .................... 435/243, 86, 42, 84, 435/85, 245, 247, 167, 252, 819, 813, 800, 253; 424/117; 210/603

[56] References Cited

U.S. PATENT DOCUMENTS

| | | | |
|---|---|---|---|
| 3,964,971 | 6/1976 | Johan et al. | 435/86 |
| 3,979,259 | 9/1976 | Johan et al. | 435/86 |
| 3,996,105 | 12/1976 | Harrison et al. | 435/42 |
| 4,119,492 | 10/1978 | Kojima et al. | 435/247 |
| 4,430,429 | 2/1984 | Zeikus et al. | 435/247 |

FOREIGN PATENT DOCUMENTS

293015 7/1929 United Kingdom ................ 435/42
748043 4/1956 United Kingdom ................ 435/42

OTHER PUBLICATIONS

Harrison, "Mixed Cultures in Industrial Fermentation Processes", *Adv. Appl. Microbiol.*, vol. 24, (1978), pp. 129–164.

*Primary Examiner*—Blondel Hazel
*Attorney, Agent, or Firm*—Karl F. Ross; Herbert Dubno; Jonathan Myers

[57] ABSTRACT

A fermentation process is disclosed for the preparation of an inoculum, suitable for batchwise, semicontinuous, or continuous production of coenzyme $B_{12}$ under septic conditions. The fermentation process begins with a broth consisting of methanol, cornsteep liquor hydrolysate or heat-treated corn slop, ammonium bicarbonate, magnesium chloride, cobalt chloride, 5,6-dimethyl-benzimidazole and sodium bisulfite used for anaerobic, mesophilic, septic fermentation production of coenzyme $B_{12}$ with anaerobic, digested sewage sludge. Fermentation is carried out over several steps to provide an inoculum containing an anaerobic, mesophilic, methane-producing, new mixed micropopulation, containing bacteria of each of the types deposited at the Hungarian National Collection of Medical Bacteria, National Institute of Hygiene, under numbers 00076, 00079, and 00272.

4 Claims, No Drawings

PROCESS FOR THE PRODUCTION OF INOCULUM FOR ANAEROBIC FERMENTATION OF COENZYME $B_{12}$

The invention relates to a process for the production of a new inoculum suitable for anaerobic formentaion of coenzyme $B_{12}$. More particularly, the invention concerns a process for the production of a new inoculum containing a new anaerobic, mesophilic, methane-producing mixed micropopulation, for use in batchwise, semicontinuous or continuous fermentation of coenzyme $B_{12}$, under septic conditions.

The term "coenzyme $B_{12}$" as used throughout the specification and claims refers not only to coenzyme B12 as such but to other biologically active corrinoids (e.g. factor III) as well (Barker et al., Biol. Chem. 235, 480 1960).

According to the literature, an inoculum is a "virus solution, microorganism or cell suspension or vegetable organ, tissue or cell used for the production of new, sterile cultures" (Straub, F. B.: *Biological Encyclopaedia* II. p. 287, Akadémiai Kiadó Budapest, 1978). The inoculum according to the invention contains an anaerobic, septic, mesophilic, methane-producing new mixed micropopulation.

Precursor as used hereinafter is a starting compound from which the desired end product is prepared by a series of biological reactions (ibid. III 437, e.g. 5,6-dimethyl-benzimidazole, cobalt chloride, etc.).

Broth is a culture medium prepared for use in the fermentation of microorganisms. The broth contains all nutrients needed by the microorganisms during fermentation in an assimilable form (ibid. IV, 249; e.g. methanol, ammonium bicarbonate, magnesium chloride, etc.). Under the term "broth" as used hereinafter we mean a culture medium containing a combination of nutrients and precursors.

Nutrients are chemical substances which are vital for the micropopulation, e.g. carbon and nitrogen sources. In the process according to the invention methanol plays a double role; it is a carbon source in the biosynthesis, and at the same time provides the energy required for the formation of mixed micropopulation.

As is known, about two decades ago coenzyme $B_{12}$ was produced by fermentation from the nutrients of sewage sludge, using the microorganisms present in the sludge. Optionally sewage sludge was supplemented with various further nutrients, too. The process was advantageous in that the fermentation could be carried out under septic conditions, but for each fermentation a large amount of sewage sludge had to be transported to the fermentation plant, the composition and bacterium population of the sludge were fluctuating, moreover so called "wild strains" could also enter the sewage sludge, by their presence making the formation of a stable bacterium population impossible.

According to the Hungarian Patent Specification No. 153,740 coenzyme $B_{12}$ was produced under anaerobic, aseptic conditions by a process in which to a broth containing the necessary nutrients sewage sludge was added only once, and after at least five inoculations, a mixed micropopulation was enriched, which could take over the role of inoculum, and produced coenzyme $B_{12}$ in an amount of about 6 to 6.2 mg/lit. of fermentation broth. This so called "sewage sludge-free" process required at least five inoculation steps to adapt the microorganisms of sewage sludge origin to produce coenzyme B12, which made the process cumbersome. In addition the coenzyme B12 production was low, a large number of different nutrients were required, accordingly, the production costs were rather high.

For the production of fermentation broths with increased coenzyme B12 content there are more processes known in the art (sec e.g. U.S. Pat. Nos. 3,964,971 and 3,979,259), which relate to the intensification of the above "sewage sludge-free" process.

A mesophilic, methane-producing mixed micropopulation was first described in the Hungarian Patent Specification No. 167,658 [Corynebacterium sp. (24A1), Corynebacterium sp. (62B9), Lactobacillus sp. (244B/C1) and Propionibacterium sp. (239 A1/6), deposited in the Hungarian National Collection of Medical Bacteria (OKI) Nation Institute of Hygiene under Nos. 00076, 00077, 00078 and 00079, respectively]. This anaerobic, mesophilic, methane-producing mixed micropopulation was, however, difficult to adapt to broths containing unconventional nutrients, six-seven inoculations were necessary. Taking into account that one inoculation cycle takes about seven days, the adaption of a fermentation based on the above micropopulation for mass production lasts for about 40 to 50 days, which is a very long time and results in high production costs.

The aim of the present invention is to eliminate the above disadvantages. To achieve the desired results, according to the invention instead of adapting an already established, above-defined anaerobic, mesophilic, methane-producing mixed micropopulation to a new broth, we returned to the sewage sludge, and from the micropopulation present therein we developed a new, anaerobic, mesophilic, methane-producing micropopulation on a broth having a completely new nutrient composition but otherwise being the same as the conventional broth. Under "conventional broth" e.g. the broth disclosed in the U.S. Pat. No. 3,964,971 is meant. The strains present in the new micropopulation were deposited in the Hungarian National Collection of Medical Bacteria (OKI) Nation Institute of Hygiene under Nos. 00076, 00079 and 00272 [Corynebacterium sp. (24 A 1): Propionibacterium sp. (239 $A_1$ /6) and Metanococcus sp. (MC-017)].

By using the new process according to the invention for the preparation of an inoculum, a new mixed micropopulation can be prepared by a single inoculation, reproducibly. Apart from using less nutrient-containing broth in place of the broth, rich in nutrients and the heat treatment (hydrolysis) of cornsteep liquor the process is advantageous in that already at the beginning essentially less living bacteria are put to the system with the broth, therefore the bacteria of the sludge used for inoculation are prevalent. The broth containing a low amount of organic substances, and having characteristically methanol as an organic component is favorable to the bacteria decomposing methanol and producing methane.

Moreover, the process according to the invention provides very secure conditions for the anaerobic, mesophilic, methane-producing, septic fermentation, since the desired micropopulation can be reproduced quickly, at low costs any time, and can then be used for the production of coenzyme $B_{12}$.

The invention relates to a process for the preparation of a new inoculum containing a new, anaerobic, mesophilic, methane-producing, mixed micropopulation suitable for the batchwise, semicontinuous or continuous fermentation of coenzyme $B_{12}$ (cobamide coenzyme).

According to this process 75 to 85 volumes/volume % of a broth containing less kinds of nutrients in a lower total concentration than the broths conventionally used for anaerobic, mesophilic, septic fermentation of coenzyme $B_{12}$ but otherwise having the same composition, is admixed with 25 to 15 volumes/volume % of anaerobic, digested sewage, the mixture is fermented for about seven days under anaerobic, mesophilic, septic conditions while adding methanol in daily amounts of 0.3 to 0.5 volumes/volume % the fermenting broth obtained (1st generation) or a portion thereof is added to a multiple—preferably four to six-fold volume of a broth having the same composition as given above, and fermentation is continued under the same conditions until the pH falls to 5 to 5.5, a portion of the fermenting broth obtained (2nd generation), preferably 5 to 15 volumes/volume % thereof, is removed and replaced by the same volume of a broth containing the same nutrients but enriched in precursor(s), and if desired, fermentation is continued for one to two further days to obtain an inoculum suitable for the production of coenzyme $B_{12}$, containing an anaerobic, mesophilic, methane-producing new mixed micropopulation.

When carrying out the process according to the invention, the broth is prepared instead of the conventionally used, commercially available nutrient component cornsteep liquor with a heat treated cornsteep liquor (hydrolysate) or corn slop.

"Corn slop" is a waste material of distillation obtained by evaporation of the combined corn steep and pot residue of distillation.

Before heat treatment cornsteep liquor is subjected to microbiological tests, and the heat treatment (hydrolysation) is carried out only on cornsteep liquor of satisfactory quality. For microbiological testing essentially the fermentation described in Example 1 is used. If on the fourth day of the test the biogas production is 0.3 to 0.6 lit./1 lit. of fermentation broth/day, the cornsteep liquor is suitable for the preparation of the new inoculum according to the invention. In this case, to the biologically qualified cornsteep liquor an equal volume of water is added, and the mixture is boiled for 15 minutes to obtain the desired heat treated cornsteep liquor (hydrolysate).

The broth used in the preparation of the new inoculum is prepared in a manner known per se (e.g. Example 1).

The broth used in the process according to the invention differs from the conventionally used broths in the followings:

it has a low organic material content, and contains characteristically methanol as an organic material, instead of commercially available cornsteep liquor it contains a heat treated solution (hydrolysate) thereof or corn slop.

As a result of new broth composition, the composition and production properties of the mixed micropopulation enriched during the preparation of inoculum are modified, and instead of 6 to 7 inoculations one inoculation and a several days' fermentation (1 to 2 days) are sufficient.

To the new broth, which contains
methanol,
cornsteep liquor hydrolysate,
ammonium bicarbonate,
magnesium chloride,
cobalt chloride,
5,6-dimethylbenzimidazole and
sodium bisulfite
15 to 25 volumes/volume % of digested sewage sludge are added. The sewage sludge is preferably taken freshly from the anaerobic post-digester of the communal sewage sludge. After thorough homogenization fermentation is started at 30° to 32° C. and is continued for about a week (until the pH falls to 5.0 to 5.5), while methanol is added and samples are taken from the fermentation broth daily. From the samples the pH and methanol content of the fermentation broth as well as the velocity of biogas production are determined. These three data are vitally important informations about the progress of fermentation. It is namely known that for the formation of the anaerobic, mesophilic, mixed micropopulation a slightly acidic medium (ph=5 to 6) is favorable. The methanol concentration of the fermentation broth is also important, since a too high or too low methanol concentration slows down the adaptation. Finally, the velocities of biogas production and methanol assimilation are important parameters, since there is a direct correlation between the methanol concentration and the velocity of the biogas production.

According to a preferred embodiment of the invention, fermentation is continued for about one week, as described above. Thereafter, the fermentation broth obtained called 1st generation, or a portion thereof is inoculated (optionally on an enlarged scale), i.e. it is added to a multiple volume of a broth. The composition of this broth is identical with that of the starting broth. Fermentation is continued for about seven additional days, essentially under the conditions described above. The fermentation broth obtained after this second fermentation period is called 2nd generation. Thereafter, about 10 volumes/volume % of the 2nd generation is replaced by an equal volume of a culture broth, which contains the same nutrients but, except methanol, 5,6-dimethylbenzimidazole and cobalt chloride, in a 10-times lower concentration.

The fermentation broth supplemented with the above fresh broth is kept at 33° to 34° C. for one or two additional days.

In this way an inoculum suitable for the initiation of B12 fermentation is obtained. The inoculum contains a new, anaerobic, mesophilic, methane-producing, mixed micropopulation.

The new inoculum according to the invention can be used in the fermentation of coenzyme $B_{12}$ as described in our co-pending Hungarian Patent Application No. 3210/83.

The process of the invention is elucidated in detail by the following, non-limiting Examples.

EXAMPLE 1

Into a laboratory-scale glass fermenter with 10 lit. working capacity 6000 ml of tap water preheated to 30° to 32° C. are added, followed by the addition of the following nutrients:
35 ml of methanol,
100 ml of a hydrolysate obtained from 50 g of cornsteep liquor,
30 g of ammonium bicarbonate,
1.0 g of magnesium chloride,
0.05 g of cobalt chloride,
0.03 g of 5,6-dimethylbenzylimidazole and
0.030 g of sodium bisulfite.

The culture broth is then thoroughly homogenized and made up to 8000 ml with tap water of 30 to 32° C. To the broth 2000 ml of a postdigested sewage sludge obtained freshly from communal sewage plant are added. The mixture is admixed, the glass fermenter is covered with a rubber plate and placed into a thermostat of 32° to 34° C.

In the following period of fermentation daily 50-ml samples are taken (after homogenization) and 35 ml of methanol are added to the fermenter, whereupon a further 200-ml sample is taken, the fermenter is covered with a rubber plate and anaerobic fermentation is continued for seven additional days, at the same temperature.

The fermentation broth obtained after the first seven days is called 1st generation.

From the sample, taken before the addition of methanol the pH and methanol concentration of the fermentation broth are determined. The 200 ml of fermentation broth removed after the addition of methanol are filled into a gasometer and the velocity of biogas production is determined. The sample is removed from the gasometer and refilled into the fermenter parallel with the addition of the next methanol portion.

On the seventh day of fermentation a 5-times increase of scale is carried out: a fermenter with 50 lit. of working capacity is filled with 30 lit. of tap water of 30° to 32° C., which is then supplemented with the following nutrients:
175 ml of methanol
500 ml of a hydrolysate obtained from 250 g of cornsteep liquor,
150 g of ammonium bicarbonate
5 g of magnesium chloride,
0.25 g of cobalt chloride,
0.15 g of 5,6-dimethylbenzimidazole,
1.5 g of sodium bisulfite.

When the addition of nutrient is complete, the broth is made up to 40 lit. with tap water of 30° to 32° C.

Thereafter, the total amount (10 lit.) of the seven day's fermentation broth (1st generation) is added to the freshly prepared broth (inoculation) and after intensive homogenization, the fermenter is sealed and anaerobic fermentation is continued at 32° to 34° C. for further seven days.

During the second seven days 50-ml. samples are taken, 175 ml of methanol are added to the fermenter and then 200 ml of samples are taken daily. The fermenter is sealed and fermentation is continued at 32° to 34° C. From the samples removed before and after the addition of methanol, respectively, the pH, methanol concentration and the velocity of biogas production are determined.

The fermentation broth obtained after the second seven days is called the 2nd generation. 10% (5.0 lit.) of the homogenized 2nd generation are removed and an equal volume of a broth having the following composition is added:
5000 ml of tap water of 30° to 32° C.,
175 ml of methanol,
50 ml of a hydrolysate obtained from 25 g of cornsteep liquor,
15 g of ammonium bicarbonate,
0.5 g of magnesium chloride,
0.25 g of cobalt chloride,
0.15 g of 5,6-dimethylbenzimidazole and
0.1 g of sodium bisulfite.

After the addition of the broth, the fermentation broth is thoroughly admixed, the fermenter is sealed and fermentation is continued at 32° to 34° C. for an additional day.

During the above procedure a new, anaerobic, mesophilic, methane-producing mixed micropopulation is formed, containing the strains deposited in the Hungarian National Collection is Medical Bacteria (OKI) National Institute of Hygiene under Nos. 00076, 00079 and 00272 [the strains following the order of deposition numbers: Corynebacterium sp. (24 A 1), Propionibacterium sp. 239 $A_1/6$) and Methanococcus sp. (MC-017)]. The inoculum is characterized by a pH of 5.4 to 5.8 and a biogas production of 0.5 to 0.8 lit. of biogas/day/lit. of fermentation broth.

The inoculum obtained is suitable for coenzyme $B_{12}$ production.

The active ingredient concentration of the fermentation broth determined from a sample taken on the first day of semicontinuous operation by the method disclosed in the Hungarian Patent Specification No. 167,658 amounts to 7.3 mg/lit.

The nutrient components are prepared as follows: Heat treatment of cornsteep liquor: Cornsteep liquor with an about 45% dry substance content is diluted with an equal volume of tap water, the mixture is brought to the boil and boiled for 15 minutes. The solution is then cooled and made up to the original volume with tap water. The fresh solution obtained is the so called heat-treated cornsteep liquor (hydrolysate).

The suitability of the cornsteep liquor used for the preparation of inoculum for active ingredient production is determined before use by the following microbiological method: Into a laboratory-scale glass fermenter with 10 lit. working capacity 9 lit. of tap water of 30° to 32° C. and subsequently the following nutrients are added:
50 ml of methanol,
50 g of untreated (unhydrolysed) cornsteep liquor containing 45% dry substance, to be tested,
30 g of ammonium bicarbonate,
1 g of magnesium chloride,
0.05 g of cobalt chloride,
0.03 g of 5,6-dimethylbenzimidazole and
0.20 g of sodium bisulfite.

After homogenization, 300 ml of fermentation broth from the coenzyme $B_{12}$ fermenter are added to the broth, which is then made up to 10 lit. with tap water of 30° to 32° C. The fermenter is covered with a rubber plate and is placed into a thermostate of 32° to 34° C. Each day 50 ml of methanol are added to the mixture after homogenization, while 200 ml of fermentation broth are removed to determine the velocity of biogas production, the fermenter is covered and fermentation is continued at 32° to 34° C. If on the 4th day of fermentation the biogas production is 0.3 to 0.6 lit./lit. of fermentation broth/day, the cornsteep liquor, after the above-described heat-treatment, is suitable for the preparation of inoculum.

5,6-dimethylimidazole is added to the broth after dissolution in the prescribed amount of methanol.

The other nutrients are directly added to the broth and dissolved therein.

EXAMPLE 2

This Example illustrates the preparation of inoculum without increasing the scale. This technique is generally employed, when a small amount of inoculum is sufficient.

Following the procedure described in Example 1, the 1st generation of inoculum is prepared in a glass fermenter with 10 lit. working capacity.

On the seventh day of fermentation (1st generation) inoculation is carried out by removing 2 lit. from the thoroughly admixed fermentation broth, and pouring it into another glass fermenter with 10 lit. working capacity. Thereafter, 6 lit. of tap water of 30° to 32° C. and then the following nutrients are added into the latter fermenter:
35 ml of methanol
100 ml of a hydrolysate obtained from 50 g of cornsteep liquor,
30 g of ammonium bicarbonate,
1 g of magnesium chloride,
0.05 g o of cobalt chloride,
0.03 g of 5,6-dimethylbenzimidazole and
0.30 g of sodium bisulfite.

When the addition of the components is complete, the mixture is thoroughly homogenized, made up to 10 lit. with tap water of 30° to 32° C., again homogenized, and the glass fermenter is covered with a rubber plate and is placed into a thermostat of 32° to 34° C.

Thereafter, a 50-ml sample is taken, 35 ml of methanol are removed and a further, 200-ml sample is removed daily, the fermenter is covered with a rubber plate, and anaerobic fermentation is continued at the same temperature for further seven days.

The fermentation broth obtained after this second seven-day period is called 2nd generation.

From the 2nd generation 10 volumes/volume % of the homogenized fermentation broth are removed and an equal volume of a broth having the following composition is introduced: Into 1.0 lit. of tap water of 30° to 32° C. the following nutrients are added:
35 ml of methanol,
10 ml of hydrolysate obtained from 5.0 g of cornsteep liquor,
3.0 g of ammonium bicarbonate,
0.1 g of magnesium chloride,
0.05 g of cobalt chloride,
0.03 g of 5,6-dimethylbenzimidazole and
0.02 g of sodium bisulfite.

After the addition of broth, the fermentation broth is thoroughly admixed, the fermenter is covered with a rubber plate, and fermentation is continued for further 24 hours, at 32° to 34° C.

The fermentation broth (inoculum) obtained after the 24-hour fermentation is suitable for use in coenzyme $B_{12}$ production.

EXAMPLE 3

This Example illustrates that the process according to the invention can be carried out also on an industrial scale.

Into a fermenter with 2.0 m³ working capacity 1000 lit. of tap water heated up to 30° to 32° C. are pumped, whereupon the following nutrients are added, after preparation as described in Example 1:
7.0 lit. of methanol,
20.0 lit. of hydrolysate obtained from 10 kg. of cornsteep liquor,
6.0 kg. of ammonium bicarbonate,
0.2 kg. of magnesium chloride,
0.01 kg. of cobalt chloride,
0.006 kg. of 5,6-dimethylbenzimidazole and
0.06 kg. of sodium bisulfite.

The broth containing the above nutrients is thoroughly homogenized, and then 400 lit. of anaerobic sewage sludge described in Example 1 are added. The mixture is made up to 2 m³ with tap water of 30° to 32° C., homogenized, the fermenter is sealed, and anaerobic fermentation is started at 30° to 32° C.

Thereafter each day sample is removed from the fermentation broth (after stirring for 20 minutes), 7.0 lit. of methanol are added, stirring is continued for 20 minutes, a further sample is removed, and fermentation is continued for 24 hours. From the sample removed before the addition of methanol the methanol concentration of fermentation broth and the pH are determined, while the sample removed after the addition of methanol is used for determining the velocity of biogas production.

On the seventh day of fermentation (1st generation) the culture is inoculated onto a fresh broth, while the scale is increased by a factor of 5. Into a fermenter with 10 m³ working capacity 6 m3 of tap water heated up to 30° to 32° C. are pumped, whereupon the following nutrients are introduced:
35.0 lit. of methanol,
100.0 lit. of a hydrolysate obtained from 50 kg. of cornsteep liquor,
30.0 kg of ammonium bicarbonate,
1.0 kg of magnesium chloride,
0.05 kg of cobalt chloride,
0.03 kg of 5,6-dimethylbenzimidazole and
0.30 kg of sodium bisulfite.

After thorough homogenization, 2 m³ of seven-day fermentation broth are pumped into the broth, which is then made up to 10 m³ with tap water of 30° to 32° C., and after homogenization, anaerobic fermentation is started at 30° to 32° C.

Furtheron, fermentation broth is stirred for 30 minutes daily, sample is taken, 35 lit. of methanol are introduced, stirring is continued for further 30 minutes and a further sample is taken.

The samples are regularly analyzed as described hereinabove.

After stirring for 40 minutes, 10 volumes/volume % of the 2nd generation fermentation broth (1 m³) are removed, and an equal volume of broth prepared as described below is introduced.

In 0.5 m³ of tap water heated up to 30° to 32° C. the following nutrients are dissolved:
35.0 lit. of methanol,
10.0 lit. of a hydrolysate obtained from 5.0 kg of cornsteep liquor,
3.0 kg of ammonium bicarbonate,
0.1 kg of magnesium chloride,
0.05 kg of cobalt chloride,
0.03 kg of 5,6-dimethylbenzimidazole and
0.02 kg of sodium bisulfite.

The above broth is introduced into the fermenter, and is then made up to 10 m³ with tap water. It is stirred for 30 minutes, whereupon stirring is terminated and anaerobic fermentation is continued for an additional 24 hours.

After 24 hours the preparation of inoculum is complete. Characteristic properties of the fermentation broth: pH=5.4 to 5.8; gas production: 0.5 to 0.8 lit./lit. of fermentation broth/day; active ingredient content: 8.3 mg/lit.

The fermentation broth obtained is suitable for use in coenzyme $B_{12}$ production.

The nutrients are prepared and the quality of cornsteep liquor is controlled as described in Example 1.

We claim:

1. A fermentation process for the preparation of an inoculum, suitable for batchwise, semi-continuous, or continuous production of Coenzyme $B_{12}$ under septic conditions, said inoculum comprising an anaerobic, mesophilic, methane-producing mixed micropopulation of bacteria strains deposited with the Hungarian National Collection of Medical Bacteria, National Institute of Hygiene under Nos. 00076, 00079 and 00272, and further comprising as nutrients and precursors: methanol, cornsteep liquor hydrolysate or heat-treated corn slop, ammonium bicarbonate, magnesium chloride, cobalt chloride, 5,6-dimethyl-benzimidazole, and sodium bisulfite; which comprises the steps of:

(a) mixing 75 to 85 vol % of a broth consisting essentially of
   methanol;
   cornsteep liquor hydrolysate or heat-treated corn slop;
   ammonium bicarbonate;
   magnesium chloride;
   cobalt chloride;
   5,6-dimethyl-benzimidazole; and
   sodium bisulfate
used for anaerobic, mesophilic septic fermentation production of Coenzyme $B_{12}$ with 15 to 25 vol % of anaerobic digested sewage sludge;

(b) fermenting the mixture found in step (a) under anaerobic, mesophilic septic conditions for about 7 days, while adding 0.3 to 0.5 vol % of methanol daily to obtain a first generation fermentation broth;

(c) adding the first generation fermentation broth or a portion thereof to a four to six fold volume of the broth defined in step (a) and continuing fermentation until the pH falls to a level of 5 to 5.5 to obtain a second generation fermentation broth;

(d) removing 5 to 15 vol % of the second generation fermentation broth daily and replacing said volume of second generation fermentation broth with an equal volume of the broth defined in step (a) but which contains additional amounts of cobalt chloride and 5,6-dimethyl-benzimidazole and (e) continuing fermentation to provide the inoculum.

2. A process as claimed in claim 1, wherein according to step (a) an aqueous solution of corn steep liquor hydrolysate is used.

3. A process as claimed in claim 1, in which 15 to 25 vol % of an anaerobic digested communal sewage sludge is added to the broth.

4. A process as claimed in claim 1, in which as anaerobic digested sewage sludge, the fresh post-digested sewage sludge of communal sewage purification plant is employed.